US012213909B2

(12) United States Patent
Steele et al.

(10) Patent No.: US 12,213,909 B2
(45) Date of Patent: Feb. 4, 2025

(54) THERMAL MANAGEMENT SYSTEM WITH SUBLIMATOR AND ADSORBENT BED

(71) Applicant: Hamilton Sundstrand Corporation, Charlotte, CT (US)

(72) Inventors: John W. Steele, New Hartford, CT (US); Peter A. Canga, League City, TX (US); Barbara M. Peyton, Windsor, CT (US); Tony Rector, East Granby, CT (US); Douglas Zupan, La Porte, TX (US)

(73) Assignee: HAMILTON SUNDSTRAND CORPORATION, Charlotte, NC (US)

( * ) Notice: Subject to any disclaimer, the term of this patent is extended or adjusted under 35 U.S.C. 154(b) by 550 days.

(21) Appl. No.: 17/388,407

(22) Filed: Jul. 29, 2021

(65) Prior Publication Data

US 2021/0353454 A1    Nov. 18, 2021

Related U.S. Application Data

(63) Continuation of application No. 15/979,673, filed on May 15, 2018, now Pat. No. 11,285,039.

(51) Int. Cl.
*A61F 7/00*        (2006.01)
*B01D 7/00*        (2006.01)
(Continued)

(52) U.S. Cl.
CPC .............. *A61F 7/0085* (2013.01); *B01D 7/00* (2013.01); *B64G 6/00* (2013.01); *C02F 9/20* (2023.01);
(Continued)

(58) Field of Classification Search
CPC . A61F 7/0085; A61F 2007/0056; B01D 7/00; B64G 6/00; C02F 1/001;
(Continued)

(56) References Cited

U.S. PATENT DOCUMENTS 3,635,216 A * 1/1972 Curtis ...................... B64G 6/00
607/104
4,587,953 A 5/1986 Rosene
(Continued)

FOREIGN PATENT DOCUMENTS

EP        3418259        12/2018
EP        3431176         1/2019

OTHER PUBLICATIONS

Steele, et al., "Efforts To Reduce International Space Station Crew Maintenance For The Management Of The Extravehicular Mobility Unit Transport Loop Water Quality," 43rd Int'l Conf. on Environ. Sys., Jul. 14-18, 2013, Vail, CO (Year: 2013).*
(Continued)

*Primary Examiner* — Patrick Orme
(74) *Attorney, Agent, or Firm* — Carlson, Gaskey & Olds, P.C.

(57) ABSTRACT

A system includes a filter device that has, in serial flow order, an adsorbent bed, a biocide filter, and a particle filter. The adsorbent bed includes adsorbent media that is configured to remove organic compounds from feed water that are capable of forming an adherent layer on a porous surface of a sublimator, and the biocide filter contains a halogen-release material.

7 Claims, 3 Drawing Sheets

(51) Int. Cl.

| | |
|---|---|
| *B64G 6/00* | (2006.01) |
| *C02F 1/28* | (2023.01) |
| *C02F 1/50* | (2023.01) |
| *C02F 9/20* | (2023.01) |
| *C02F 103/02* | (2006.01) |
| *F24F 5/00* | (2006.01) |
| *C02F 1/00* | (2023.01) |
| *C02F 101/32* | (2006.01) |
| *C02F 101/34* | (2006.01) |

(52) U.S. Cl.
CPC .... *F24F 5/0035* (2013.01); *A61F 2007/0056* (2013.01); *C02F 1/001* (2013.01); *C02F 1/283* (2013.01); *C02F 1/50* (2013.01); *C02F 2101/322* (2013.01); *C02F 2101/34* (2013.01); *C02F 2101/40* (2013.01); *C02F 2103/023* (2013.01); *C02F 2303/04* (2013.01)

(58) Field of Classification Search
CPC .... C02F 1/283; C02F 1/50; C02F 9/20; C02F 2101/322; C02F 2101/34; C02F 2101/40; C02F 2103/023; C02F 2303/04; F24F 5/0035
See application file for complete search history.

(56) References Cited

U.S. PATENT DOCUMENTS

| | | | |
|---|---|---|---|
| 6,080,313 A * | 6/2000 | Kelada | C02F 9/20 210/266 |
| 6,423,219 B1 | 7/2002 | Chandler | |
| 8,753,523 B2 | 6/2014 | Harris | |
| 8,980,097 B2 | 3/2015 | Theivendran et al. | |
| 9,394,185 B2 | 7/2016 | Rector et al. | |
| 11,285,039 B2 * | 3/2022 | Steele | B64G 1/50 |
| 2004/0195181 A1 | 10/2004 | Loftis | |
| 2005/0181931 A1 * | 8/2005 | Mouri | B01J 20/28004 502/60 |
| 2011/0002086 A1 * | 1/2011 | Feaver | H01G 11/32 252/511 |
| 2011/0114573 A1 | 5/2011 | Simpson et al. | |
| 2013/0306195 A1 | 11/2013 | Steele | |
| 2017/0121186 A1 | 5/2017 | Fichtner | |
| 2017/0320765 A1 | 11/2017 | Bigelow et al. | |

OTHER PUBLICATIONS

Adam, N., Cox, T., Larner, K., Carter, D., Kouba, C. (2017). Evaluation and certification of Ambersorb 4652 for use in activated carbon ion exchange filters for the International Space Station. 47th International Conference on Environmental Systems. Jul. 16-20, 2017. p. 1.

Steele, J.W., Etter, D., Rector, T., Boyle, R., and Vandezande, C. (2014). Efforts to reduce International Space Station crew maintenance for the management of the extravehicular mobility unit transport loop water quality. Retrieved from: https://ntrs.nasa.gov/search.jsp?R=20130011190 2019-01-04T16:04:22+00:00Z.

Lewis, J.F., Cole, H., Gronin, G., Gazda, D.B., and Steele, J. (2006). Extravehicular Mobility Unit (EMU)/International Space Station (ISS) coolant loop failure and recovery. Society of Automotive Engineers, Inc. Jul. 17, 2006. pp. 1-9.

Rector, T., Metselaar, C., Peyton, B., Steele, J., Michalek, W., Bowman, E., Wilson, M., Gazda, D., et al. (2014). An evaluation of technology to remove problematic organic compounds from the International Space Station potable water. 44th International Conference on Environmental Systems. Jul. 13-17, 2014. Tuscon, AZ. pp. 1-15.

Steele, J.W., Etter, D., Rector, T., Hill, T., and Wells, K. (2012). Management of the post-shuttle Extravehicular Mobility Unit (EMU) water circuits. Jan. 1, 2012. Retrieved from: https://ntrs.nasa.gov/archive/nasa/casi.ntrs.nasa.gov/20120003778.pdf.

Steele, J., Elms, T., Peyton, B., and Rector, T. (2016). Redesign of the Extravehicular Mobility Unit airlock cooling loop recovery assembly. 46th International Conference on Environmental Systems. Jul. 10-14, 2016. Vienna, Austria.

Kumar, A., Prasad, B., and Mishra, I.M. (2010). Isotherm and kinetics study for acrylic acid removal using powdered activated carbon. Journal of Hazardous Materials. Issue 176. pp. 774-783.

Juang, R-S., Lee, W-C., and Chen, C-L. (2004). Removal of sodium dodecyl benzene sulfonate and phenol from water by a combined PAC adsorption and cross-flow microfilteration process. Journal of Chemical Technology and Biotechnology. Issue 79. pp. 240-246.

* cited by examiner

THERMAL MANAGEMENT SYSTEM WITH SUBLIMATOR AND ADSORBENT BED

CROSS-REFERENCE TO RELATED APPLICATION

The present disclosure is a continuation of U.S. patent application Ser. No. 15/979,673 filed May 15, 2018.

STATEMENT REGARDING FEDERALLY SPONSORED RESEARCH OR DEVELOPMENT

This invention was made with government support under contract number NNJ10TB01C awarded by NASA. The government has certain rights in the invention.

BACKGROUND

A sublimator is a primary cooling device for the Extravehicular Mobility Unit (EMU) spacesuit. The sublimator includes a metallic porous plate that is exposed to space vacuum on one side and is supplied with expendable feed water on the other side. The feed water freezes on the porous plate surface. The vacuum side progressively sublimes the ice to the vacuum of space to remove waste heat from the astronaut that is introduced into the plate.

The feed water may contain trace organic compound contaminants, typically from wetted non-metallic materials in the feed water loop (primarily amphipathic long-chain organic acids, fatty acids and surfactants with carboxylate functional groups), external water reservoirs, and transfer plumbing, which can deposit on the metallic plate. Such a deposit may be in the form of an adherent molecular monolayer. This monolayer can impede sublimation and, therefore, debit sublimator performance.

The organic compounds may include processing aids, as exemplified by abietic acid, from EMU Neoprene Latex feed-water bladders, sodium dodecyl benzene sulfonate (a candidate soap for International Space Station-ISS processed water), acrylic acid oligomers from the ISS Water Processor multi-filtration bed sorbents, or other amphipathic compounds.

It is theorized that the hydrophilic "heads" of the amphipathic compounds anchor or adhere to available cationic charge on the metallic surface of the porous plate, and that the hydrophobic "tails" of the amphipathic molecules form an intertwined monolayer. This phenomenon does not occur with non-volatile contaminants, such as corrosion products, iodine and biofilm, which do not have the structural features of an amphipathic compound. These non-amphipathic contaminants readily dislodge from the effluent side of the porous plate during the sublimation process and have minimal effect on performance.

SUMMARY

A system according to an example of the present disclosure includes a filter device that has, in serial flow order, an adsorbent bed, a biocide filter, and a particle filter. The adsorbent bed includes adsorbent media that is configured to remove organic compounds from feed water that are capable of forming an adherent layer on a porous surface of a sublimator, and the biocide filter contains a halogen-release material

BRIEF DESCRIPTION OF THE DRAWINGS

The various features and advantages of the present disclosure will become apparent to those skilled in the art from the following detailed description. The drawings that accompany the detailed description can be briefly described as follows.

DETAILED DESCRIPTION

Figure 1:
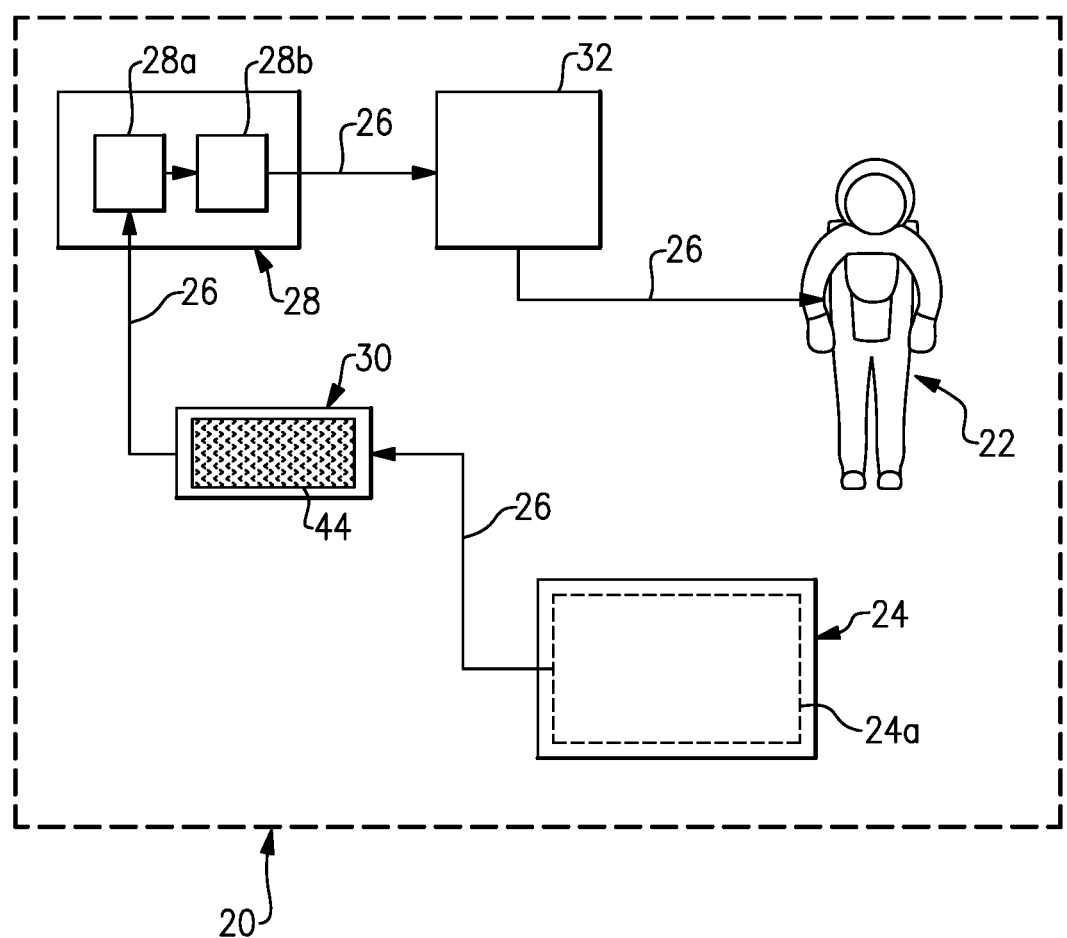
FIG. 1 illustrates an example thermal management system that has a feed water container, filter device with an adsorbent bed, a pump unit, and a space structure with a sublimator.

FIG. 1 schematically illustrates an example of a thermal management system 20 ("system 20"). As will be described, the system 20 includes features for removing organic compound contaminants from feed water used in the system 20—compounds which could otherwise form an adherent layer on a key component and impede performance of the system 20.

The system 20 includes a space structure 22, a feed water container 24, a water feed line 26, a pump unit 28 with pump 28a, and a filter device 30. The water feed line 26 generally fluidly connects the container 24 with the space structure 22. The pump unit 28 and the filter device 30 are disposed in the water feed line 26, with the filter device 30 located upstream of the pump unit 28 between the pump unit 28 and the container 24.

In this example, the pump unit 28 also includes a valve 28b, and there is an umbilical interface assembly 32 between the pump unit 28 and the space structure 22, although these may vary or be excluded depending on the implementation application of the system 20. In the illustrated example, the space structure 22 is a space suit, such as an Extravehicular Mobility Unit (EMU) spacesuit. However, it is to be appreciated that the space structure 22 is not limited to space suits and that the space structure 22 may alternatively be a space vehicle, spacecraft, or other structure designed for use and operable in the environment of outer space.

Figure 2:
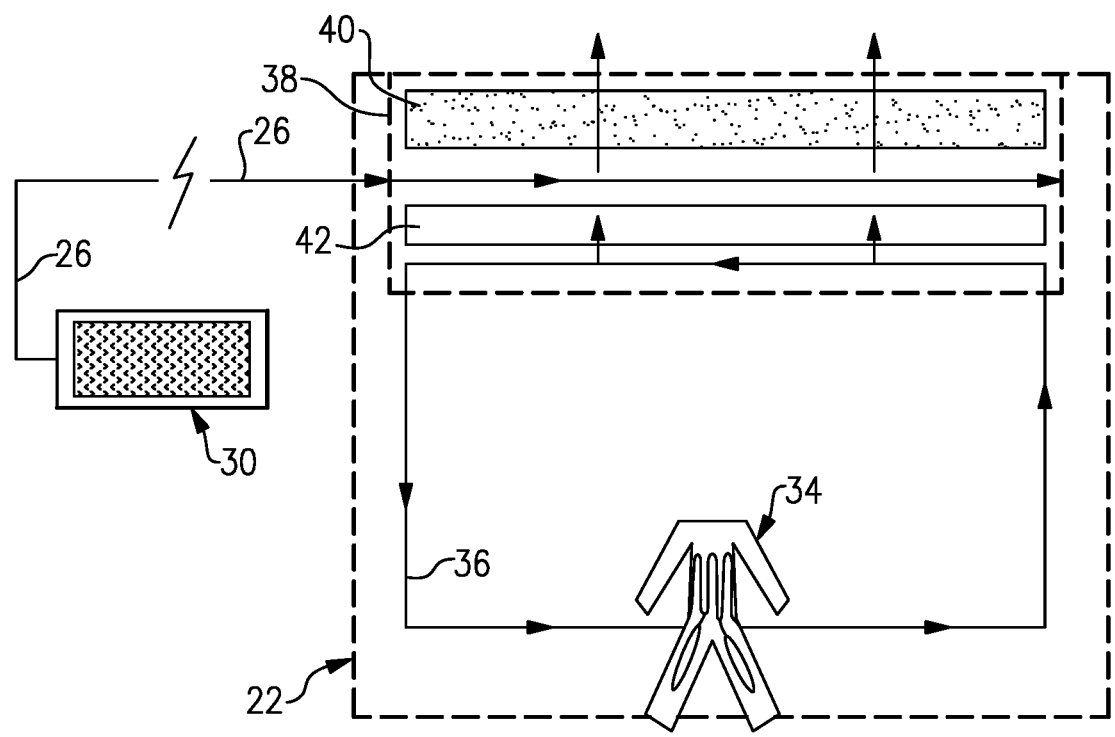
FIG. 2 schematically illustrates portions of an example of a space structure.

The space structure 22 is also shown schematically in FIG. 2. The space structure 22 includes a heat source 34 connected with a fluid loop 36 for conveying a working fluid through the heat source 34 to regulate temperature. The heat source 34 may be, but is not limited to, one or more hardware components in the space structure 22 that generate heat or a garment that collects heat from a wearer of the garment (astronaut). Most typically the working fluid will be water, but other working fluids could alternatively be used.

The space structure 22 includes a sublimator 38 that is connected with the fluid loop 36 to receive the working fluid there though. The sublimator 38 includes a porous surface 40, such as a porous metal plate or a porous fibrous structure, and a heat conduction member 42. The porous surface 40 is exposed on one side to a vacuum, which in most implementations is the vacuum of outer space. Feed water from the container 24 is provided via water feed line 26 into the sublimator 38. The sublimator 38 is operable via the porous surface 40 to freeze and sublime the feed water to the vacuum. Waste heat from the fluid loop 36 is introduced into the sublimator 38 through the heat conduction member 42. The heat conduction member 42 transfers the heat into the feed water adjacent the porous surface 40. The heat is removed via the sublimation process of the feed water at the porous surface 40.
}

The container 24 stores the feed water before delivery to the space structure 22. As an example, the container 24 includes a reservoir 24a, formed of a fluoropolymer or stainless steel, which serves to provide a sterile containment vessel for the feed water. The pump unit 28 and the filter device 30 in the water feed line 26 serve to deliver and treat the feed water from the container 24.

If organic compounds are present in the feed water, the compounds can deposit on the porous surface 40 of the sublimator 38 and debit performance. The filter device 30 serves to facilitate removal of organic compounds. The filter device 30 includes one or more adsorbent beds 44 that are configured to substantially remove target organic compounds from the feed water that are capable of forming an adherent layer on the porous surface 40. For example, "substantial removal" is a reduction of at least one of the target organic compounds, or even more desirably of multiple target organic compounds, by at least 50% in a single pass. In one further example, "substantial removal" presumes a maximum total organic carbon of 2 parts-per-million in the influent water and a reduction of the total organic carbon by 75% or more to 0-0.5 parts-per-million. Example target organic compounds that can form adherent layers in the sublimator 38 include abietic acid, sodium dodecyl benzene sulfonate (SDBS), acrylic acid oligomers, hexadecanoic acid, or n-butyl benzene sulfonamide (NBBS).

Figure 3:
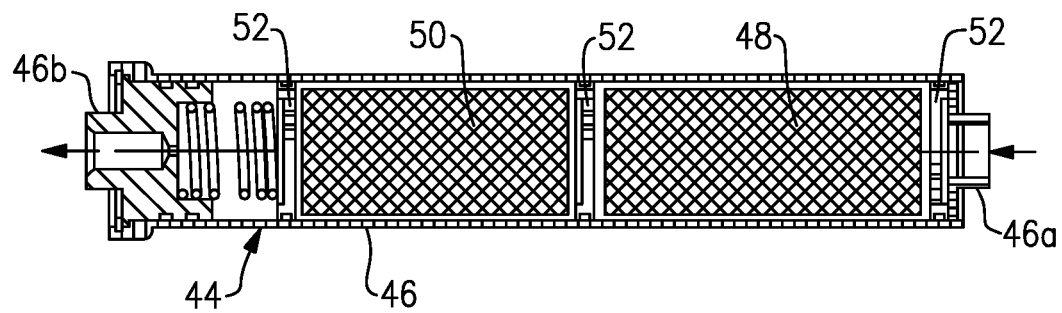
FIG. 3 illustrates an example adsorbent bed a adsorbent media.

FIG. 3 illustrates an example of the adsorbent bed 44 of the filter device 30. The adsorbent bed 44 includes a housing 46 that defines an inlet or influent side 46a and an outlet or effluent side 46b. The influent and effluent sides 46a/46b designate the structure of the inlet and outlet, respectively, but these terms are also used to refer to the ends of the adsorbent bed 44 through which the feed water enters and exits the adsorbent bed 44. In this example, the adsorbent bed 44 includes first and second adsorbent media 48/50. The adsorbent media 48/50 may be retained in the housing 46 via screens 52, with a biasing member (e.g., a spring) facilitating retention and compaction of the adsorbent media 48/50.

The first and second adsorbent media 48/50 are different with regard to adsorption capability of the target organic compounds that can form an adherent layer and impede sublimation. For instance, the first and second adsorbent media 48/50 are different with regard to adsorption capability of at least two of abietic acid, sodium dodecyl benzene sulfonate (SDBS), acrylic acid oligomers, hexadecanoic acid, or n-butyl benzene sulfonamide (NBBS). In other words, the first adsorbent media 48 may be superior for removing compound A but poor for removing compound B, and the second adsorbent media 50 may be superior for removing compound B but poor for removing compound A. In this manner, the adsorbent media 48/50 are complimentary. Adsorption capability may be measured by the amount of a particular contaminant removed by a preset amount of media under a preset flow rate over the media for a preset amount of time. A Total Organic Carbon Monitor device may be used to provide a sum of all organics in the water. Gas Chromatography-Mass Spectrometry may be used to identify specific organic compounds. As will be appreciated, the adsorbent bed 44 may alternatively include only one type of adsorbent media if there is a single organic compound of interest or if the adsorbent media has good adsorption capability for the organic compounds of interest.

The following examples are directed to the first and second adsorbent media 48/50, however, it is to be understood that any of the adsorbent media described herein can also be used alone as the sole media of the adsorbent bed 44.

In one example, the first and second adsorbent media 48/50 are activated carbon (also known as activated charcoal) that are capable of substantially removing the target organic compounds, such as those listed above, that are capable of forming an adherent layer on the porous surface 40. For instance the first adsorbent media 48 is a synthetic activated carbon and the second adsorbent media 50 is a natural activated carbon. Synthetic activated carbon is typically formed by controlled pyrolysis of a polymer precursor. Natural activated carbon is typically formed by controlled pyrolysis of naturally occurring materials, such as coal, lignite, nutshells, and flour. Alternative adsorbents may be or may include zeolites, which are microporous aluminosilicate materials.

One example of the synthetic activated carbon that is capable of substantially removing the target organic compounds has pore size of less than two nanometers, a specific surface area of 1400 $m^2/g \pm 10\%$, a mean grain size of 600 micrometers±10%, ash content by weight of 0.4%, and an apparent density of 0.4 $g/cm^3 \pm 10\%$. One further example of the synthetic activated carbon is AMBERSORB® 4652 (trademark registered to Rohm and Haas Company). The physical characteristics of grade 4652 are hereby incorporated by reference.

One example natural activated carbon that is capable of substantially removing the target organic compounds is formed from steam activation of coal, a specific surface area of 1150 $m^2/g \pm 10\%$, a grain size of +8 mesh/−30 mesh, ash content by weight of 8%, and an apparent density of 0.49 $g/cm^3 \pm 0.03$. Further examples of the natural activated carbon are NORIT® Darco 8x30 and NORIT® Darco 20x40 (trademark registered to Norit International N.V.). The physical characteristics of grades Darco 8x30 and 20x40 are hereby incorporated by reference.

In another example, the adsorbent bed 44 includes, by volume of a total amount of the first and second adsorbent media 48/50, from 40% to 60% of the first adsorbent media 48 and from 60% to 40% of the second adsorbent media 50. For instance, the adsorbent bed 44 may include 40%, 45%, 50%, 55% or 60% of the first adsorbent media 48 and, respectively, 60%, 55%, 50%, 45%, or 40% of the second adsorbent media 50.

In one example, the adsorbent bed 44 contains only synthetic activated carbon, and excludes other types of adsorbents. Although the addition of natural activated carbon may offer a wider range of compounds that are removed, natural activated carbon may also have the side effect of releasing small amounts of chlorides, which can leads to corrosion of downstream metal components (e.g., the metal plate of the sublimator 38). In implementations that utilize a metal plate in the sublimator 38, the adsorbent bed 44 may thus contain only synthetic activated carbon.

In another example, the adsorbent media 48/50 is synergistically arranged in the adsorbent bed 44 with respect to flow through the adsorbent bed 44. For instance, it was found that the second adsorbent media 50 (natural activated carbon) is superior for adsorbing acrylic acid oligomers. Adsorption of other organic compounds may reduce capability of the second adsorbent media 50 for adsorbing acrylic acid oligomers. To preserve the adsorption capacity of the second adsorbent media 50 for acrylic acid oligomers, the first adsorbent media 48 (synthetic activated carbon) is located on the influent side 46a and the second adsorbent media 50 (natural activated carbon) is on the effluent side 46b. The first adsorbent media 48 removes sodium dodecyl benzene sulfonate (SDBS) and n-butyl benzene sulfonamide (NBBS), which could otherwise diminish capacity of the second adsorbent media 50 for adsorbing the acrylic acid oligomers. In this manner, the first adsorbent media 48 buffers the second adsorbent media 50 to preserve adsorption capacity for the acrylic acid oligomers.

Figure 4:
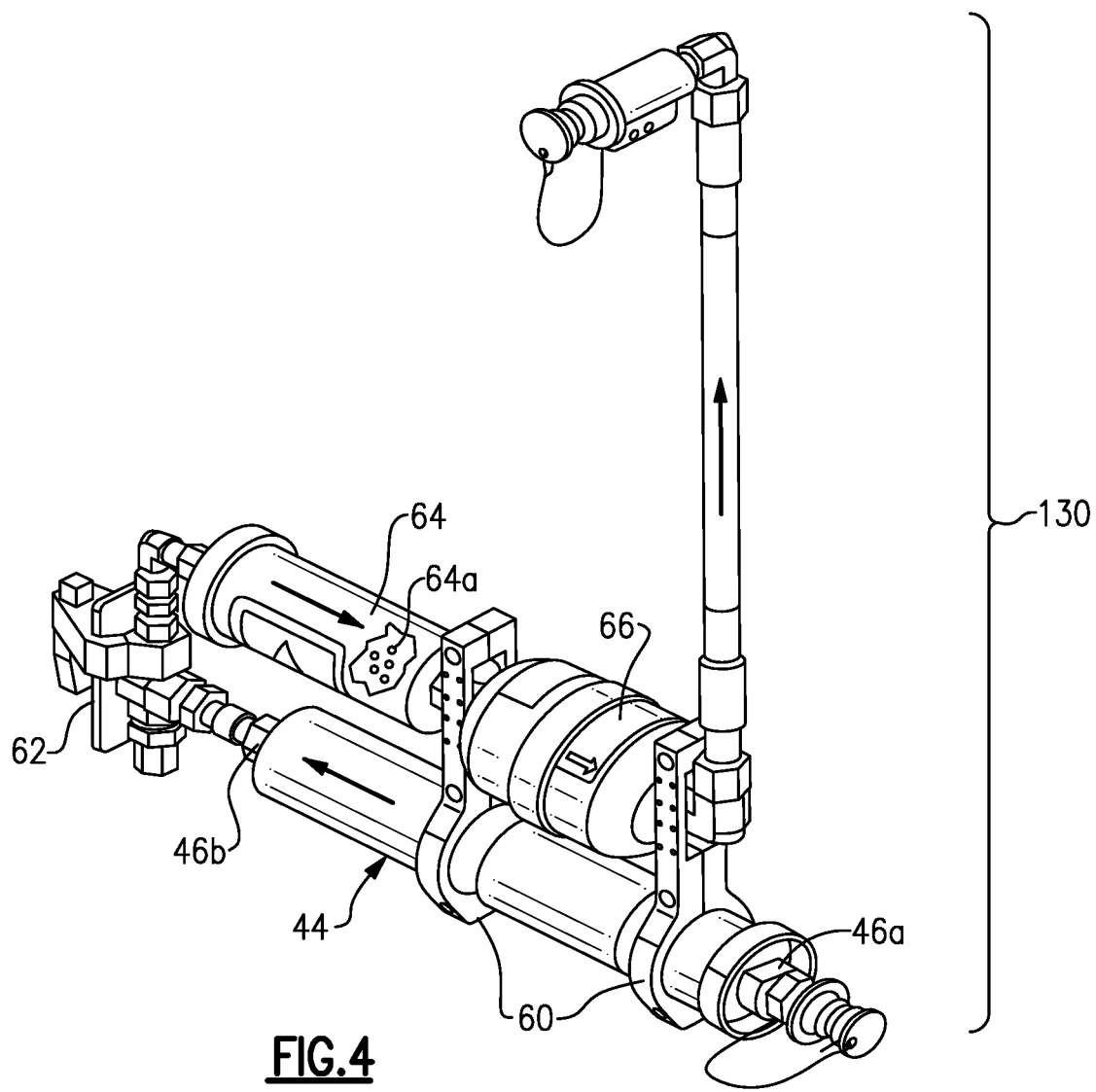
FIG. 4 illustrates an example filter device for use in the system of FIG. 1.

FIG. 4 illustrates an example of a filter device 130 for use in the system 20 in addition to or in place of the filter device 30. In this example, the filter device 130 includes the adsorbent bed 44 as described above. The adsorbent bed 44 is held in one or more support yokes 60. The outlet 46b of the adsorbent bed 44 is connected with a valve 62, such as a three-way ball valve. The valve 62 may be operated manually to open and close flow through the filter device 130. Alternatively, the valve 62 may be an automated valve that does not require direct manual operation to open and close.

A biocide filter 64 is connected immediately downstream of the valve 62. The biocide filter 62 includes a halogen-release material 64a. The feed water is typically pretreated to contain iodine or other biocide. The adsorbent bed 44, in addition to removing organic compounds, may as an unintended consequence also remove the biocide. The biocide filter 64 serves to release biocide, such as iodine or other halogen, into the feed water to replenish the biocide that was removed by the adsorbent bed 44.

A particle filter 66 is located immediately downstream from the biocide filter 64. As an example, the particle filter 66 includes a mesh or screen to catch and thereby remove particles from the feed water. In one example, the mesh or screen is a 3-micron filter or smaller. A 3-micron filter is capable of capturing particles of greater than 3 micrometers or larger. In the filter device 130, particles of the adsorbent media 48/50 may escape from the adsorbent bed 44. The particle filter 66 serves to catch those particles, as well as other particles that may be in the feed water, so that the particles do not interfere with the pump unit 28, the sublimator 38, or other downstream structures.

The one or more support yokes 60 also support the biocide filter 64 and the particle filter 66. In this example, the biocide filter 64 and the particle filter 66 are co-linear to each other. Further, the biocide filter 64 and the particle filter 66 are parallel with, and adjacent to, the adsorbent bed 44. Such an arrangement provides a retrograde or counterflow configuration. That is, the incoming feed water flow through the adsorbent bed 44 in one direction, and the outgoing feed water flows through the biocide filter 64 and the particle filter 66 in the opposite direction. This provides a relatively compact package envelope, which is of particular advantage in space structures that demand efficient use of design space.

In addition to purifying the feed water for use in the sublimator 38, the location of the filter device 130 also benefits the pump unit 28 and the umbilical interface assembly 32. The filter device 130 is located upstream of the pump unit 28 and the umbilical interface assembly 32. Thus, the removal of organic compounds by the filter device 130 also facilitates reduction in fouling of these components.

The system 20 also demonstrates an example of a method for providing clean feed water. The method may include, at a position upstream of the pump 28a in the system 20, removing organic compounds from the feed water that are capable of forming an adherent layer on the porous surface 40 of the sublimator 38.

A further example implementation of the method and the system 20 in a space environment, such as the International Space Station, may include the following steps.

Connect the container 24 to the inlet 46a of the adsorbent bed 44.

Connect the outlet 46b of the adsorbent bed 44 to the pump unit 28.
Open the valve 62 on the filter device 30/130.
Open the valve 28b on the pump unit 28.
Power up the space structure 22, if not already powered (e.g., a spacesuit).
Turn on power to the pump unit 28.
Turn the pump 28a on to deliver the feed water to the space structure 22.
Once finished, terminate power to the pump 28a.
Turn off power to the pump unit 28.
Power down the space structure 22.
Close the valve 28b.
Close valve 62.
Disconnect the filter device 30/130 from the pump unit 28.
Disconnect the container 24 from the filter device 30.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from this disclosure. The scope of legal protection given to this disclosure can only be determined by studying the following claims.

What is claimed is:

1. A system comprising:
a filter device including, in serial flow order, an adsorbent bed, a biocide filter, and a particle filter, wherein the adsorbent bed includes adsorbent media that is configured to remove organic compounds from feed water that are capable of forming an adherent layer on a porous surface of a sublimator, and the biocide filter contains a halogen-release material, the adsorbent bed including first and second adsorbent media, the first adsorbent media is synthetic activated carbon that has a specific surface area of 1400 $m^2/g \pm 10\%$ and an apparent density of 0.4 $g/cm^3 \pm 10\%$, and the second adsorbent media is natural activated carbon that has a specific surface area of 1150 $m^2/g \pm 10\%$ and an apparent density of 0.49 $g/cm^3 \pm 0.03$, and the adsorbent bed including a housing defining an influent side and an effluent side, the first adsorbent media is located on the influent side, and the second adsorbent media is located on the effluent side.

2. The system as recited in claim 1, wherein the adsorbent bed, biocide filter, and particle filter are held in one or more support yokes.

3. The system as recited in claim 1, further comprising a valve between the biocide filter and the adsorbent bed.

4. The system as recited in claim 1, wherein the adsorbent media includes from 40% to 60% of synthetic activated carbon and from 60% to 40% of natural activated carbon.

5. The system as recited in claim 1, further comprising:
a space structure including a heat source connected with a fluid loop for conveying a working fluid through the heat source to regulate temperature and the sublimator connected with the fluid loop to receive the working fluid, the sublimator having a porous surface;
a feed water container;

a water feed line connected with the feed water container and the porous surface of the sublimator;

a pump in the feed water line and operable to move the feed water from the feed water container to the porous surface of the sublimator, wherein the sublimator is operable to cool the working fluid by freezing and subliming the feed water using the porous surface; and the filter device being located in the water feed line between the pump and the feed water container, the filter device operable to remove organic compounds from the feed water that are capable of forming an adherent layer on the porous surface.

6. The system as recited in claim 5, wherein the space structure is a spacesuit.

7. The system as recited in claim 5, wherein the organic compounds include one or more of abietic acid, sodium dodecyl benzene sulfonate (SDBS), acrylic acid oligomers, hexadecanoic acid, or n-butyl benzene sulfonamide (NBBS).

* * * * *